United States Patent [19]

Roth

[11] Patent Number: 5,441,513
[45] Date of Patent: Aug. 15, 1995

[54] RETRACTING TIP TROCAR ASSEMBLY

[75] Inventor: Alex T. Roth, Foster City, Calif.

[73] Assignee: United States Surgical Corporation, Norwalk, Conn.

[21] Appl. No.: 850,089

[22] Filed: Mar. 12, 1992
(Under 37 CFR 1.47)

[51] Int. Cl.$^6$ .............................................. A61B 5/00
[52] U.S. Cl. .................................. 606/185; 128/770
[58] Field of Search ............... 606/167, 185; 604/158, 604/164, 165, 167, 169, 264, 272

[56] References Cited

U.S. PATENT DOCUMENTS

| | | |
|---|---|---|
| 1,213,001 | 1/1917 | Philips . |
| 2,496,111 | 1/1950 | Turkel . |
| 2,623,521 | 12/1952 | Shaw . |
| 3,030,959 | 4/1962 | Grunert . |
| 3,605,744 | 9/1971 | Dwyer . |
| 3,643,649 | 2/1972 | Amato . |
| 3,657,812 | 4/1972 | Lee . |
| 3,817,251 | 6/1974 | Hasson . |
| 3,882,849 | 5/1975 | Jamshidi . |
| 3,904,033 | 9/1975 | Haerr . |
| 4,018,228 | 4/1977 | Goosen . |
| 4,168,699 | 9/1979 | Hauser . |
| 4,177,814 | 12/1979 | Knepshield et al. . |
| 4,207,887 | 6/1980 | Hiltebrandt et al. . |
| 4,210,246 | 7/1980 | Banko . |
| 4,220,155 | 9/1980 | Kimberling et al. . |
| 4,254,762 | 3/1981 | Yoon . |
| 4,256,119 | 3/1981 | Gauthier . |
| 4,299,230 | 10/1981 | Kubota . |
| 4,356,826 | 11/1982 | Kubota . |
| 4,375,815 | 2/1983 | Burns . |
| 4,393,587 | 7/1983 | Kloosterman . |
| 4,411,653 | 10/1983 | Razi . |
| 4,414,974 | 11/1983 | Dotson et al. . |
| 4,499,898 | 2/1985 | Knepshield et al. . |
| 4,535,773 | 8/1985 | Yoon .................................. 604/169 |

(List continued on next page.)

FOREIGN PATENT DOCUMENTS 0067743 12/1982 European Pat. Off. .
0265193 4/1988 European Pat. Off. .
WO89/03661 5/1989 WIPO .

(List continued on next page.)

OTHER PUBLICATIONS

F. S. Zubairov, "Needle for the Puncture and Lavage of the Abdominal Cavity" (Russian with English Translation).
Hartenberg and Denavit, *Kinematic Synthesis of Linkages*, p. 10 (1964).
Barton, *Mechanism Analysis*, pp. 1–5 and 261 (1984).
Hiscox, *Mechanical Movements*, pp. 70 and 118 (1907).
Barber, *Engineer's Sketch* Book, pp. 56–57, 78–79 and 112–113 (1890).
Mable and Reinholtz, *Mechanisms and Dynamics of Machinery*, 4th ed., pp. 1–2 (1987).
Beggs, *Mechanism*, pp. 384–385 (1955).
Grafstein and Schwarz, Pictoral Handbook of Technical Devices, p. 141 (1971).
Chironis, *Mechanisms & Mechanical Devices Sourcebook*, pp. 94, 115, 137, 147 and 444 (1991).
Marks' Standard Handbook for Mechanical Engineers, 8th Edition, pp. 8–3 and 8–4 (1978).

*Primary Examiner*—Stephen C. Pellegrino
*Assistant Examiner*—Nancy Mulcare

[57] ABSTRACT

A retracting tip trocar assembly including a trocar tube and a shaft having a piercing tip at one end thereof. The device includes a retracting mechanism which allows the piercing tip to be held in a cutting position upon application of an insertion force such as when the piercing tip is pressed against a wall of a human body cavity. Upon release of the insertion force, such as when the piercing tip passes through the wall, the retracting mechanism causes the piercing tip to be retracted into the trocar tube.

34 Claims, 4 Drawing Sheets

U.S. PATENT DOCUMENTS

| | | |
|---|---|---|
| 4,552,559 | 11/1985 | Donaldson et al. . |
| 4,556,059 | 12/1985 | Adamson, Jr. . |
| 4,559,041 | 12/1985 | Razi . |
| 4,601,710 | 7/1986 | Moll . |
| 4,637,393 | 1/1987 | Ray . |
| 4,642,099 | 2/1987 | Phillips et al. . |
| 4,653,475 | 3/1987 | Seike et al. . |
| 4,654,030 | 3/1987 | Moll et al. ............... 606/185 |
| 4,664,654 | 5/1987 | Strauss . |
| 4,723,545 | 2/1988 | Nixon et al. . |
| 4,730,613 | 3/1988 | Gordy . |
| 4,733,662 | 3/1988 | DeSatnick et al. . |
| 4,747,831 | 5/1988 | Kulli . |
| 4,813,940 | 3/1989 | Parry . |
| 4,817,631 | 4/1989 | Schnepp-Pesch et al. . |
| 4,850,973 | 7/1989 | Jordan et al. . |
| 4,869,717 | 9/1989 | Adair . |
| 4,874,375 | 10/1989 | Ellison . |
| 4,902,280 | 2/1990 | Lander . |
| 4,911,693 | 3/1990 | Paris . |
| 4,919,653 | 4/1990 | Martinez et al. . |
| 4,931,042 | 6/1990 | Holmes et al. . |
| 4,940,458 | 7/1990 | Cohn . |
| 4,943,280 | 7/1990 | Lander . |
| 4,955,870 | 9/1990 | Ridderheim et al. . |
| 4,958,625 | 9/1990 | Bates et al. . |
| 4,973,316 | 11/1990 | Dysarz . |
| 4,986,814 | 1/1991 | Burney et al. . |
| 4,994,042 | 2/1991 | Vadher . |
| 5,009,643 | 4/1991 | Reich et al. . |
| 5,013,294 | 5/1991 | Baier . |
| 5,030,206 | 7/1991 | Lander ................ 606/185 |
| 5,046,508 | 9/1991 | Weissler . |
| 5,049,136 | 9/1991 | Johnson . |
| 5,059,184 | 10/1991 | Dyke . |
| 5,066,288 | 11/1991 | Deniega et al. ............ 604/164 |
| 5,073,169 | 12/1991 | Raiken . |
| 5,092,853 | 3/1992 | Couvertier, II . |
| 5,104,382 | 4/1992 | Brinkerhoff et al. . |
| 5,104,383 | 4/1992 | Shichman . |
| 5,114,407 | 5/1992 | Burbank ................ 606/185 |
| 5,116,353 | 5/1992 | Green ................. 606/184 |
| 5,127,909 | 7/1992 | Shichman . |
| 5,152,754 | 10/1992 | Plyley et al. ............ 604/164 |
| 5,158,552 | 10/1992 | Borgia et al. ............ 604/165 |
| 5,196,025 | 3/1993 | Ranalletta et al. .......... 606/182 |
| 5,224,951 | 7/1993 | Freitas ................ 606/185 |
| 5,226,426 | 7/1993 | Yoon .................. 604/169 |
| 5,246,425 | 9/1993 | Hunsberger et al. ........ 604/272 |

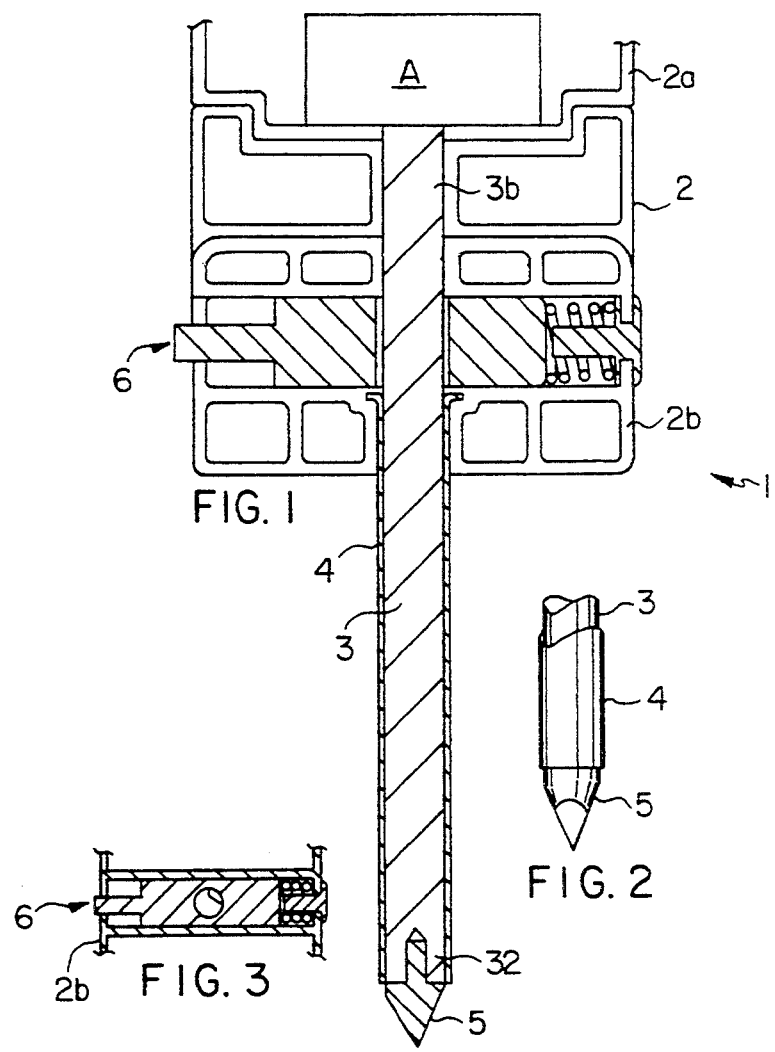
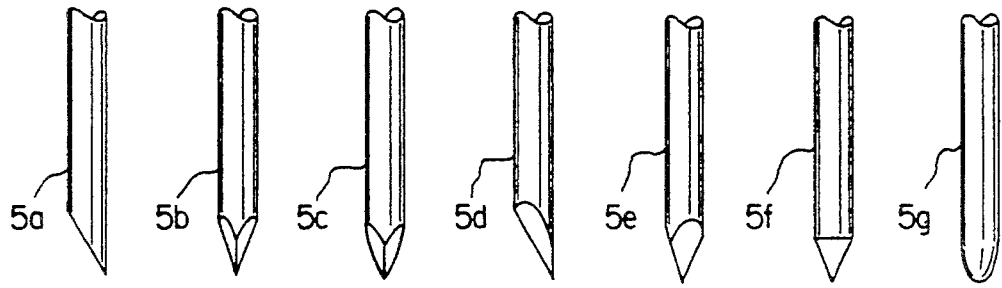
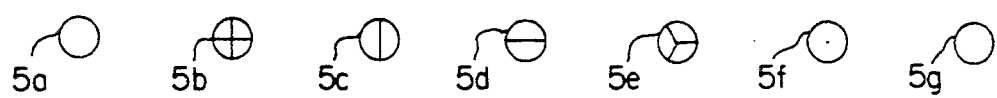

RETRACTING TIP TROCAR ASSEMBLY

FIELD OF THE INVENTION

The invention relates to surgical instruments. More particularly, it relates to a retracting tip trocar assembly with an improved protective shield latch.

BACKGROUND OF THE INVENTION

Trocars are sharp-pointed instruments used to puncture a body cavity. A body cavity is often punctured so that fluids may be drained using a cannula inserted into the opening. Trocars are also used during endoscopic procedures. A conventional endoscopic procedure follows three steps. The first step is the insertion of a Veress cannula into an abdominal cavity through a small incision in the abdominal wall. The second step is the inflation of the cavity with insufflating gas passed through the cannula. After inflation, the Veress cannula is removed. The third step is the thrusting of standard trocar housed within the bore of a trocar tube into the inflated abdomen. Standard trocars are shaped like a large metal peg with a sharpened point. The trocar is then removed, and the endoscopic instrument is inserted into the abdominal cavity through the trocar tube.

U.S. Pat. Nos. 4,601,710 (the '710 patent) and 4,654,030 (the '030 patent), the disclosures of which are hereby incorporated by reference, describe embodiments of a trocar assembly having a spring-biased tubular protective shield. One of the embodiments in the '710 patent has a shield locking mechanism that comprises a slide valve-actuated locking tooth that engages a slot in the wall of the shield. The '030 patent discloses an embodiment wherein the flap valve functions as a shield locking means wherein a tip seats against a recessed shoulder on the shield. The valve is manually controlled to release the shield.

Trocar assemblies having spring-biased tubular protective shields include a tubular protective shield within a trocar tube. In addition, once the piercing tip of the obturator penetrates a wall of a body cavity, the protective shield must further widen the opening created by the piercing tip before the protective shield can move outwardly of the trocar tube to shield the piercing tip which remains in the body cavity. U.S. Pat. No. 4,535,773 (the '773 patent) discloses a reusable trocar wherein the obturator can be retracted by means of a spring and an electromechanical latching mechanism. In particular, the piercing tip of the obturator includes pressure sensing means which transmits signals to activate a solenoid which in turn releases the obturator shaft so that it can be retracted. The retractable obturator disclosed in the '773 patent requires a complex arrangement wherein sliding contacts and circuitry are used to energize a solenoid which removes a detent which is biased into engagement with a sliding part of the obturator. Such an arrangement is costly and could be unreliable due to bad connections in the electrical circuitry.

It would be desirable to provide a disposable trocar assembly wherein the piercing tip can be retracted automatically after piercing the wall of the body cavity by a purely mechanical arrangement. Such a retractable tip trocar assembly would provide advantages over the tubular protective shield arrangement of the '710 and '030 patents since the trocar tube could be used to shield the obturator, thereby eliminating the need for the protective tubular shield.

SUMMARY OF THE INVENTION

The invention provides a retracting tip trocar assembly comprising an elongated trocar obturator extending in an axial direction and having a piercing tip at a distal end thereof and an elongated trocar tube in which the trocar obturator is housed. The piercing tip is movable in the axial direction from a cutting position (at which the piercing tip is outside a distal end of the trocar tube) to a shielded position (at which the piercing tip is entirely within the trocar tube). The assembly includes retracting means for retracting the piercing tip from the cutting position to the shielded position when a force applied to the piercing tip is removed and a member which is movable from a first position (at which the member prevents movement of the trocar obturator) to a second position (at which the member does not prevent movement of the trocar obturator). The member is held in the first position when the piercing tip is pressed against an object with an axial force above a threshold value, and the assembly includes biasing means biasing the member in the second position. The biasing means applies a bias force on the member such that when the insertion force is below the threshold value, the member moves from the first position to the second position and the retracting means moves the piercing tip to the shielded position.

The retracting means can be activated by release of an insertion force load placed on the piercing tip during insertion of the piercing tip into a wall of a body cavity with release of the insertion force load activating the retracting means to automatically retract the piercing tip. The insertion force load can comprise a compressive load acting in an axial direction parallel to a longitudinal axis of the trocar tube.

The assembly can include a trocar handle housing, and the trocar obturator can include a shaft having a distal end thereof attached to the piercing tip and a proximal end thereof attached to the trocar handle housing. The retracting means can comprise spring means for biasing the piercing tip in the shielded position, and the member can comprise link means for holding the piercing tip in the cutting position while the insertion force load is placed on the piercing tip. The link means can comprise first and second links, the first link having one end thereof pivotally attached to the proximal end of the shaft and the other end thereof pivotally attached to one end of the second link. The other end of the second link can be pivotally attached to the trocar handle housing such that the links are in a first configuration when the piercing tip is in the cutting position and in a second configuration when the piercing tip is in the shielded position.

The spring means can comprise a spring such as a torsion spring which moves the links into the second configuration when the insertion force load is released. The link means can include a stop means in the trocar handle housing for sustaining the insertion force load which acts axially on the piercing tip. The shaft and the first and second links can be aligned axially to support the insertion force load when the piercing tip is in the cutting position and the piercing tip is pushed against a wall of a body cavity. The first and second links can include abutting surfaces which press against each other when the piercing tip is in the cutting position. For example, the first and second links comprise a single piece of plastic material, and the abutting surfaces can be connected by a bendable section of the plastic material.

The link means can comprise a deformable link which has a first configuration when the piercing tip is in the cutting position and a second configuration when the piercing tip is in the shielded position. The biasing means can comprise a spring which biases the deformable link in the second configuration. The deformable link can include two rigid sections hinged together intermediate opposite ends of the deformable link with the opposite ends of the deformable link being moved closer together when the piercing tip moves to the shielded position.

The retracting tip assembly can include latch arm means on one of the links for manually moving the links to the first configuration. The trocar handle housing can also include catch means for holding the latch arm means in an armed position where the piercing tip is in the cutting position. The latch arm means can comprise a latch arm having one end thereof connected to one of the links and the other end thereof extending external to the trocar handle housing. The catch means can comprise a curved slot in the trocar handle housing with the latch arm being movable along the curved slot. The curved slot can terminate in an enlarged opening formed in part by a support surface against which the latch arm presses when the piercing tip is in an armed position. In this way, the piercing tip can be located further outside the distal end of the trocar tube in the armed position than when the piercing tube is in the cutting position. Also, the latch arm will automatically move from the support surface to a position in alignment with the curved slot when the piercing tip is pushed against an object such as a wall of a body cavity.

The trocar handle housing can include a track, and the shaft can include a slider which cooperates with the track to guide the shaft axially along the trocar tube. The spring can comprise a wire having first and second arms extending from a coiled portion of the wire such that the first arm presses against the first link and the second arm presses against the second link. The spring can also comprise a torsion spring which applies a torsional restraining force on the piercing tip. In this case, the spring causes the piercing tip to rotate when the retracting means moves the piercing tip from the cutting position to the shielded position.

The invention also provides a method of puncturing a wall of a human body cavity, comprising a step of providing a retractable tip trocar assembly having an elongated trocar obturator extending in an axial direction and having a piercing tip at a distal end thereof, an elongated trocar tube in which the trocar obturator is housed such that the piercing tip is movable in the axial direction from a cutting position at which the piercing tip is outside the trocar tube to a shielded position at which the piercing tip is entirely within the trocar tube, retracting means for retracting the piercing tip from the cutting position to the shielded position when the piercing tip punctures a wall of a human body cavity, a member movable from a first position at which the member prevents movement of the trocar obturator to a second position at which the member does not prevent movement of the trocar obturator and biasing means biasing the member in the second position. The member is held in the first position when the piercing tip is pressed against an object with an axial force above a threshold value, and the biasing means applies a bias force on the member such that when the insertion force is below the threshold value the member moves from the first position to the second position and the retracting means moves the piercing tip to the shielded position. The method also includes a step of piercing the wall of a human body cavity by manually pushing the piercing tip against the wall of the human body cavity until the piercing tip punctures the wall and the retracting means withdraws the piercing tip entirely into the trocar tube. The method can include insufflating the human body cavity before or after the piercing step.

The trocar assembly can include a housing, and the retracting means can include link means and spring means biasing the link means in a bent configuration, the link means being extendible to a straight configuration and including a latch arm extending through a slot in the housing and the slot having a catch along the length thereof. The method can include an arming step comprising moving the latch arm along the slot to extend the link means to the straight configuration and engaging the latch arm with the catch to hold the piercing tip in the cutting position.

The latch arm can be flexible and automatically disengaged with the catch during the piercing step due to axial movement of the link means when an insertion load force is placed on the piercing tip.

The housing can include an upper housing and a lower housing with the trocar obturator and retracting means being supported by the upper housing. The upper housing can be separable from the lower housing, and the lower housing can include a valve such as a trumpet valve or a flap valve for automatically sealing the trocar tube when the trocar obturator is removed from the trocar tube. The method can further include a step of separating the upper housing from the lower housing such that the trocar tube is sealed by the valve after the piercing step is performed.

BRIEF DESCRIPTION OF THE DRAWING

FIG. 1 shows a cross-section of a retractable tip trocar assembly in accordance with the invention;

FIG. 2 shows a cut-away perspective view of the lower end of the trocar assembly shown in FIG. 1;

FIG. 3 shows a partial cross-section of a trumpet valve forming part of the assembly shown in FIG. 1;

FIGS. 8-21 show various configurations for the piercing tip;

DETAILED DESCRIPTION OF THE INVENTION

Figure 4:
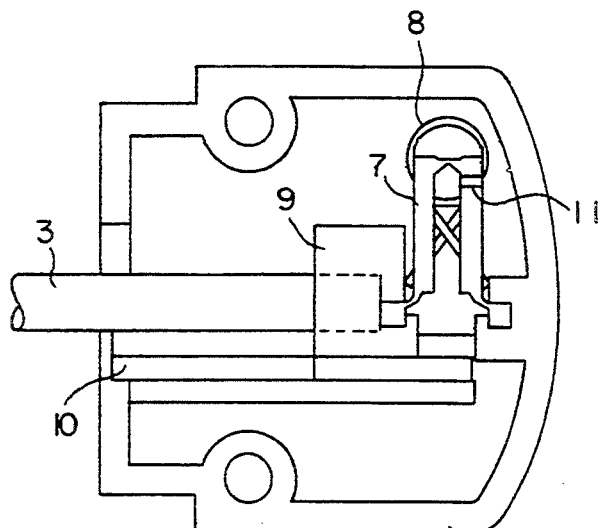
FIG. 4 shows a cross-section of an upper housing of the trocar assembly shown in FIG. 1 wherein the piercing tip is in a shielded position.

A trocar is a device for introducing a sleeved portal into a body cavity. If the trocar has a piercing tip, the tip can cause trauma to the cavity tissues either by direct over thrust or by side-to-side laceration. The device can be made safer if, when the piercing tip penetrates through the cavity wall, the piercing tip can be made to automatically and quickly retract into the trocar tube.

One way to trigger the retraction is to rely upon the release of the insertion force load on the piercing tip of the trocar assembly upon passage through the cavity wall. Once this restraining load is released, the piercing tip is free to move through another position to one wherein a spring force can pull it back within the trocar tube. This restraining force acting on the piercing tip can be compressive along the longitudinal axis of the trocar or torsional around the same axis.

A linear retracting tip trocar in accordance with the invention can be constructed as follows. The piercing tip is attached to a shaft that can translate linearly in the trocar tube. At the handle end, the shaft is attached by a pivot to a short link. The other end of this link is pivotally attached to a second link. The other end of this second link is pivotally attached to the trocar handle. Range of motion allowed by the geometrical set-up of the links grants freedom of movement of the piercing tip from a retracted ("shielded") position well within the confines of the trocar tube to an extended ("cutting") position with the tip extending beyond the end of the trocar tube. A spring acts on the links to bias the linkage such that the piercing tip is in the shielded position.

If the shaft is extended (against spring force) from the shielded position wherein the links are retractable to one wherein the links are fully extended and then is retracted a short distance but with the links buckled in the opposite direction against a stop, the shaft and piercing tip will sustain a compressive load. If this compressive load is maintained, as in the instance of insertion of the piercing tip through a cavity wall tissue, when the restraint is released (full insertion), the spring will cause the links to elongate and extend the shaft a short distance before fully retracting the piecing tip into the trocar tube.

This mechanism can be simplified if the two links are constructed as a single "living hinge" plastic part. Such a hinge should be sufficiently flexible to hinge at the pivot positions yet sufficiently rigid to sustain the compressive insertion forces. However, any arrangement wherein a member supports the insertion force load in one position and is biased to move to a position at which the obturator can be retracted when the insertion force falls below a threshold value can be used in accordance with the invention.

The second link can include a spring latch arm which is stiff in one direction of bending so that it allows rotation of the link and subsequent extension of the shaft and piecing tip. This latch arm protrudes through a curved slot in the trocar handle allowing manual access to the latch arm. The latch arm can spring in a direction normal to the actuating slot so that in the extended position it can be shifted into a side latched position, thus holding the piercing tip in the extended position. This would be akin to an "armed" condition.

In usage, the user would manually slide the latch arm around the slot and into the latched "armed" position. When pressure is initially applied on the piercing tip against tissue, the latch will slide back into the main curved slot, but the compressive load applied to the point of the shaft will hold the shaft and links in a locked yet extended position. When the piercing tip breaks through the cavity wall, the compressive restraint force is removed thereby allowing the spring to advance the piercing tip a small amount as the links bend and then to retract it into the trocar tube.

It is within the scope of the invention to use a torsion acting device which would work in a similar fashion but would require a torsional restraining force on the piercing tip with a corresponding rotational displacement required to shift the shaft into a position wherein it could be withdrawn into the trocar tube. In this case, the piercing tip will spin as it retracts into the trocar tube.

The retraction spring force in either case must be strong enough to ensure quick and positive retraction. The mechanism should be contained within the trocar handle so that the mechanism, the shaft, and the piercing tip can be removed as a unit from the trocar tube when the trocar tube is placed in position.

The embodiments described above are "metastable retracting tip" type trocars. "Metastable" refers to the two stability points of the positions of the piercing tip, the less stable being the extended position which goes to a more stable position, the retracted position, upon sensing a change in loading.

Various embodiments of the retractable trocar tip assembly will now be described with reference to FIGS. 1–29.

FIG. 1 shows a retractable tip trocar assembly 1 in accordance with the invention. The assembly 1 includes a housing 2 including an upper housing 2a and a lower housing 2b. The upper housing 2a supports a shaft 3 having a distal end 3a and a proximate end 3b, and the lower housing 2b supports a trocar tube 4 such that the shaft 3 fits within the trocar tube 4. The upper housing 2a is separable from the lower housing 2b so that the shaft 3 can be withdrawn from the trocar tube 4. A mechanism A is provided for retracting the shaft 3 during use of the assembly 1.

A piercing tip 5 is provided at the distal end 3a of the shaft 3. Valve means such as a trumpet valve 6 or flap valve (not shown) is provided in the lower housing 2b for automatically sealing the trocar tube 4 when the shaft 3 is removed therefrom. FIG. 3 shows a partial cross-section of the trumpet valve 6.

The piercing tip 5 can be integral with the shaft 3 or can comprise a separate part, as shown in FIG. 1. Various shapes of the piercing tip 5 are shown in FIGS. 8–21. For instance, FIG. 8 shows a side view of a hypo-tip 5a, and FIG. 9 shows an axial end view thereof. FIG. 10 shows a nail-type piercing tip 5b, and FIG. 11 shows an axial end view thereof. FIG. 12 shows a rounded chisel-tip 5c, and FIG. 13 shows an axial end view thereof. FIG. 14 shows an offset two-facet tip 5d, and FIG. 15 shows an axial end view thereof. FIG. 16 shows a pyramidal three-facet tip 5e, and FIG. 17 shows an axial end view thereof. FIG. 18 shows a conical tip 5f, and FIG. 19 shows an axial end view thereof. FIG.

20 shows a bullet point tip 5g, and FIG. 21 shows an axial end view thereof.

FIG. 4 shows a cross-section of one embodiment of the upper housing 2a wherein the retracting mechanism A includes retracting means, a member and biasing means. The retracting means moves the piercing tip from the cutting position to the shielded position. The member is movable from a first position (at which the member prevents movement of the trocar obturator) to a second position (at which the member does not prevent movement of the trocar obturator), the member being held in the first position when the piercing tip is pressed against an object with an axial force above a threshold value. The biasing means biases the member in the second position, the biasing means applying a bias force on the member such that when the insertion force is below the threshold value the member moves from the first position to the second position and the retracting means moves the piercing tip to the shielded position. For instance, the member can comprise link means 7, and the retraction means and biasing means can comprise spring means 8.

Figure 6:
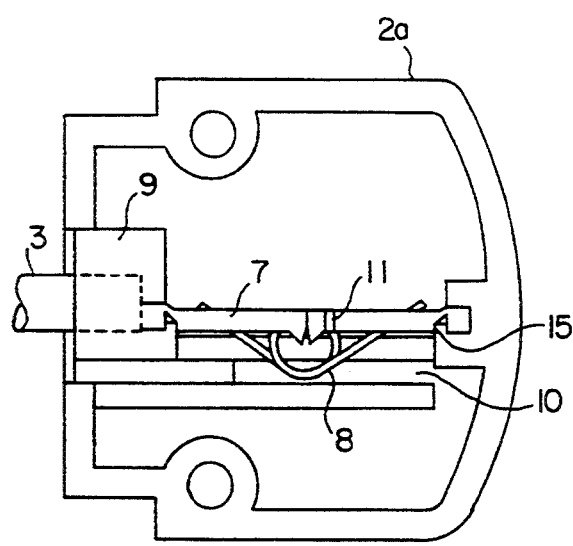
FIG. 6 is a cross-section of the upper housing wherein the piercing tip is in a cutting position.
Figure 7:
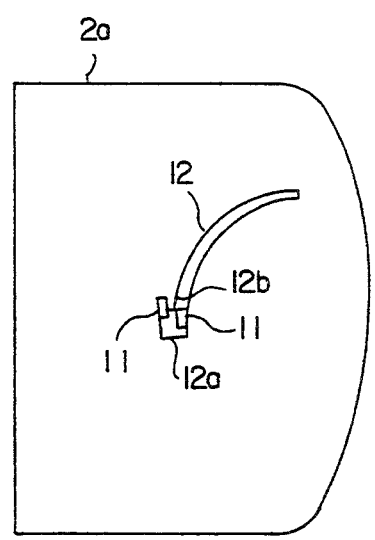
FIG. 7 shows a perspective view of the upper housing shown in FIG. 6 wherein the latch arm is in a position corresponding to the cutting position.

As shown in FIG. 4, the shaft 3 is movably supported by means of the link means 7, the spring means 8 and a slider 9. The slider 9 slides in a track 10, and the link means 7 is bendable from a first bent configuration, as shown in FIG. 4, to a second straight configuration, as shown in FIG. 6. The link means 7 includes a latch arm 11 extending through a slot 12 in the upper housing 2a.

Figure 5:
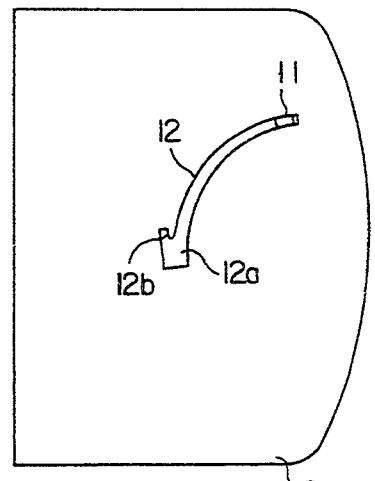
FIG. 5 shows a perspective view of the upper housing wherein a latch arm is in a position corresponding to the shielded position of the piercing tip.

As shown in FIG. 5, the slot 12 is curved and includes an enlarged portion 12a and a catch 12b. To arm the trocar assembly, the latch arm 11 is moved along the slot until it engages the catch 12b, as shown in dotted lines in FIG. 7. However, when an insertion force load is applied to the shaft 3, the link means 7 is compressed in the axial direction and the latch arm 11 disengages from the catch 12b and moves to a position at which it is free to move along the slot 12. When the piercing tip 5 punctures a wall of a cavity, the insertion force is released, and the force of the spring 8 deforms the link means 7 into the bent configuration shown in FIG. 4.

The link means 7 includes a first link 13 and a second link 14. Links 13 and 14 can comprise a single piece of material, such as a plastic material, or they can comprise two or more discrete links which are connected together in a manner which will support the insertion force load but allow the shaft 3 to move axially when the insertion force load falls below a threshold value, such as upon breakthrough of a cavity wall.

Figure 23:
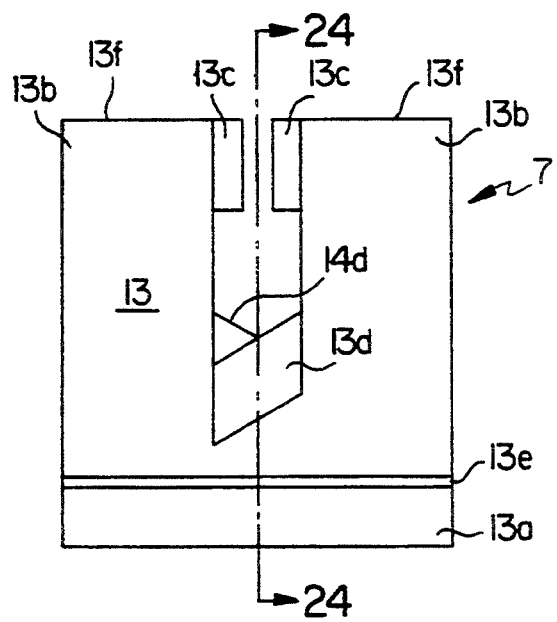
FIG. 23 shows a perspective end view of the deformable link.

As shown in FIGS. 6 and 23, the upper housing 2a includes a stop 15 which engages one end of the link means 7 when an insertion force is applied to the piercing tip 5. The first link 13 includes a first end 13a and a second end 13b. In addition, the link 13 is U-shaped, as shown in FIG. 23. The link 13 includes surfaces 13c for engaging a coil of the spring means 8. The link 13 also includes an inclined surface 13d for engaging one arm of the spring means 8. In order to accommodate shrinkage and extension in the axial direction, the link 13 includes a flexible portion 13e. The link 13 also includes a surface 13f for abutting a similar surface 14f on the link 14.

Figure 24:
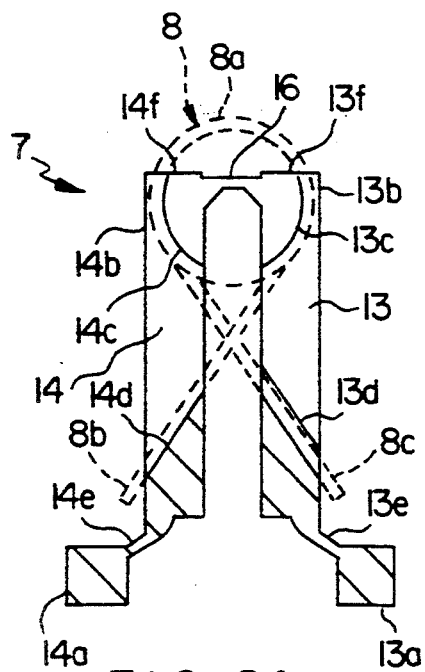
FIG. 24 shows a cross-section of the deformable link taken along the line 24—24 in FIG. 23.

The link 14 is similar to the link 13 and includes portions 14a–f as described above with reference to link 13. As shown in FIG. 24, the spring means 8 is supported such that the coil thereof fits around surfaces 13c, 14c and the arms of the spring press against surfaces 13d and 14d. The end 14a of link 14 fits into a corresponding recess in slider 9, and the end 13a of link 13 fits into a corresponding recess in the upper housing 2a.

Figure 22:
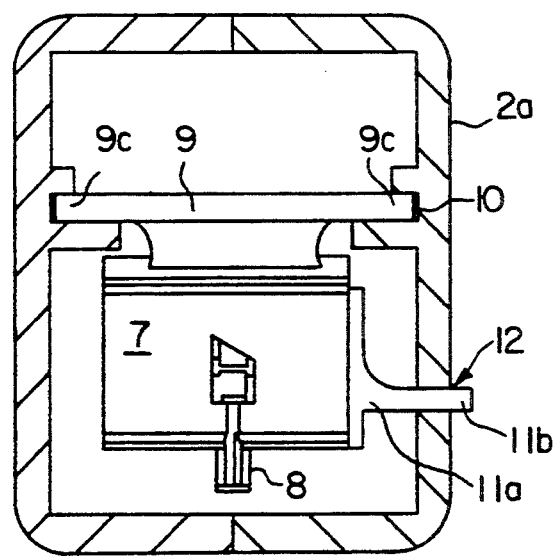
FIG. 22 shows a lateral cross-section of the upper housing wherein a deformable link is in a bent configuration.
Figure 25:
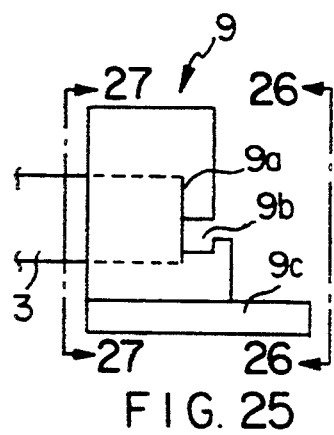
FIG. 25 shows a side view of a slider.
Figure 26:
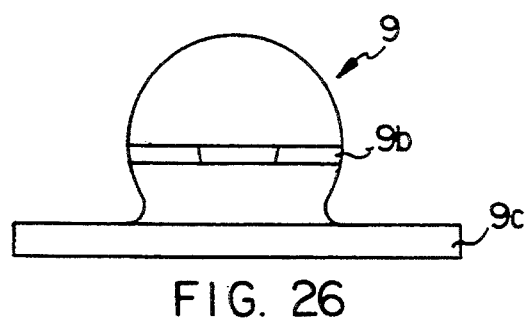
FIG. 26 shows a perspective axial end view of the slider shown in FIG. 25 taken along the line 26—26.
Figure 27:
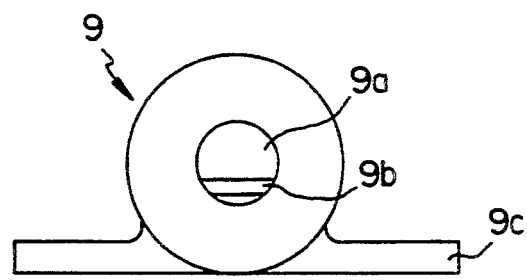
FIG. 27 is a perspective axial end view of the slider shown in FIG. 25 taken along the line 27—27.

The slider 9 is shown in FIGS. 25–27. As can be seen in FIG. 25, the slider 9 includes a bore 9a in which the proximal end of the shaft 3 is fixedly secured. The slider 9 also includes recess 9b for receiving end 14a of link 14. The slider 9 also includes a foot 9c which rides in track 10, as shown in FIG. 22. FIG. 26 is a front view of the slider 9 from the direction facing recess 9b, and FIG. 27 is a rear view of the slider 9 from the direction of the bore 9a.

Figure 28:
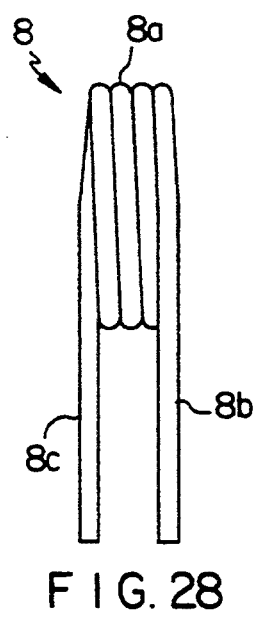
FIG. 28 is a side view of a spring.
Figure 29:
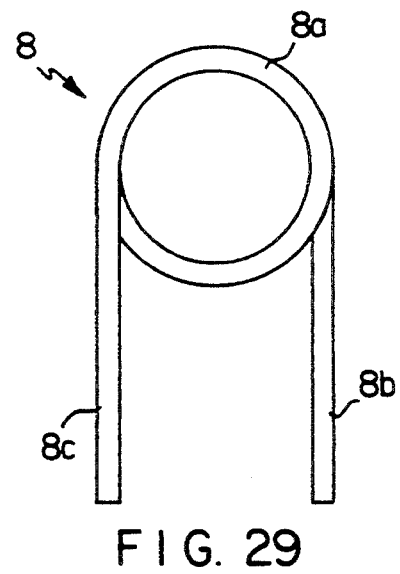
FIG. 29 is a front view of the spring shown in FIG. 28.

Details of the spring means 8 are shown in FIGS. 28 and 29. In particular, the spring means 8 can comprise a torsion spring formed from a coil of wire 8a and a pair of rectilinearly extending arms 8b, 8c, extending from each end of the coil 8a. As shown in FIGS. 28 and 29, the arms 8b and 8c are parallel to each other, and each is tangent to the coil 8a on opposite sides of the coil 8a. As shown in FIG. 24, the arms 8b, 8c are crossed such that they press against surfaces 13d, 14d of links 13, 14. In this manner, the links 13, 14 are biased toward each other so as to maintain the piercing tip 5 in the shielded position. However, when the piercing tip 5 is placed in the armed or cutting position, the arms 8b, 8c are bent to the position shown in FIG. 6.

As explained earlier, upon application of an insertion force to the piercing tip 5, the shaft 3 is retracted slightly in the axial direction so as to press the link means 7 against the stop 15. When the insertion force is released, such as when the piercing tip punctures a wall of a human body cavity, the force of the spring 8 deforms the link means 7 such that it assumes the position shown in FIG. 4. The link means 7 is capable of extending slightly when the piercing tip is in the armed position and shrinking slightly when the piercing tip is in the cutting position due to the provision of flexible portions 13e, 14e. During retraction of the piercing tip, the links 13, 14 will extend slightly when the abutting surfaces 13f, 14f initially separate, after which the links 13, 14 move toward each other to retract the shaft 3.

In the mechanism A described above, spring 8 is effective for bending links 13, 14 from a straight configuration (as shown in FIG. 6) to a bent configuration (as shown in FIG. 4). Alternatively, a different type of mechanism A could be used. For instance, the mechanism could include a torsion spring which is arranged such that the spring is unwound in the axial direction when the piercing tip is placed in the cutting or armed position. The device would operate as described earlier, that is, upon application of an insertion force, the spring would be held in its extended position, but when the insertion force is released, the spring would retract in the axial direction while rotating and moving the piercing tip to the shielded position.

While the invention has been described with reference to the foregoing embodiments, various changes and modifications can be made thereto which fall within the scope of the appended claims.

What is claimed is:

1. A retracting tip trocar assembly comprising:
   an elongated trocar obturator extending in an axial direction and having a proximal end and a piercing tip at a distal end thereof;
   an elongated trocar tube in which the trocar obturator is housed, the piercing tip being movable in the axial direction from a cutting position at which the piercing tip is outside a distal end of the trocar tube to a shielded position at which the piercing tip is entirely within the trocar tube;

a trocar handle housing which receives the proximal end of the elongated trocar obturator and which includes a catch;

a first link pivotally attached to the trocar obturator and to a second link, the second link being pivotally attached to the trocar handle housing, the links being in a first configuration when the piercing tip is in a cutting position outside the distal end of the trocar tube and the links being in a second configuration when the piercing tip is in the shielded position; and retracting means mounted within the trocar handle for retracting the piercing tip from the cutting position to the shielded position, the retracting means acting on at least one of the first and second links;

wherein the catch releasably maintains the links in the first configuration.

2. The retracting tip assembly of claim 1, wherein said links are movable from said first configuration, at which the links prevent movement of the trocar obturator, to said second configuration, at which the links do not prevent movement of the trocar obturator, the links being held in the first configuration when the piercing tip is pressed against an object with an axial insertion force above a threshold value, said retracting means comprises biasing means for applying a bias force on at least one of said links such that the biasing means moves the at least one of said links from the first configuration to the second configuration when the axial insertion force is below the threshold value upon release of the axial insertion force placed upon the piercing tip while the piercing tip is in the cutting position, to retract the piercing tip to the shielded position.

3. The retracting tip assembly of claim 2, wherein the insertion force comprises a compressive load acting in an axial direction parallel to the axial direction of tip movement.

4. The retracting tip assembly of claim 1, wherein the retracting means comprises a spring engaged with at the least one of said links and biasing the links toward the second configuration, wherein one end of said first link is pivotally attached to a proximal end of said trocar obturator, another end of said first link is pivotally attached to an end of said second link, and another end of said second link is pivotally attached to said trocar housing.

5. A retracting tip trocar assembly comprising:

an elongated trocar obturator extending in an axial direction and having a proximal end and a piercing tip at a distal end thereof;

an elongated trocar tube in which the trocar obturator is housed, the piercing tip being movable in the axial direction from a cutting position at which the piercing tip is outside a distal end of the trocar tube to a shielded position at which the piercing tip is entirely within the trocar tube;

a trocar handle housing which receives the proximal end the elongated trocar obturator and which includes a catch;

a member movable from a first position at which the member prevents movement of the trocar obturator to a second position at which the member does not prevent movement of the trocar obturator, the member being held in the first position when the piercing tip is held against an object with an axial force above a threshold value, wherein the member comprises first and second links for holding the piercing tip in the cutting position while the insertion force load is placed on the piercing tip, the first link pivotally attached to the trocar obturator and to the second link, the second link being pivotally attached to the trocar handle housing, the links being in a first configuration when the piercing tip is in the cutting position and the links being in a second configuration when the piercing tip is in the shielded position; and at least one spring mounted within the trocar handle housing for retracting the piercing tip from the cutting position to the shielded position;

wherein the catch releasably maintains the links in the first configuration and said at least one spring applies a bias force on at least one of said links such that when the insertion force is below the threshold value, upon release of the axial insertion force placed on the piercing tip while the piercing tip is in the cutting position, the links move from the first configuration to the second configuration and the piercing tip moves to the shielded position.

6. The retracting tip assembly of claim 5, wherein the spring is engaged with at least one of the links and biases the links toward the second configuration, wherein one end of said first link is pivotally attached to a proximal end of said trocar obturator, another end of said first link is pivotally attached to an end of said second link, and another end of said second link is pivotally attached to said trocar housing.

7. The retracting tip assembly of claim 1, further comprising a stop in the trocar handle housing for sustaining the insertion force which acts axially on the piercing tip, the trocar obturator and the first and second links being aligned substantially axially and supporting the insertion force against the stop when the piercing tip is in the cutting position and the piercing tip is pushed against an object.

8. The retracting tip assembly of claim 1, wherein the first and second links include abutting surfaces which press against each other when the piercing tip is in the cutting position.

9. The retracting tip assembly of claim 8, wherein the first and second links comprise a single piece of plastic material.

10. The retracting tip trocar assembly of claim 9, wherein the single piece of plastic comprises two plastic links connected by a bendable section of the plastic material.

11. A retracting tip trocar assembly comprising:

an elongated trocar obturator extending in an axial direction and having a proximal end and a piercing tip at a distal end thereof;

an elongated trocar tube in which the trocar obturator is housed, the piercing tip being movable in the axial direction from a cutting position at which the piercing tip is outside a distal end of the trocar tube to a shielded position at which the piercing tip is entirely within the trocar tube;

a trocar handle housing which receives the proximal end of the elongated trocar obturator and which includes a catch;

a member movable from a first position at which the member prevents movement of the trocar obturator to a second position at which the member does not prevent movement of the trocar obturator, the member being held in the first position when the piercing tip is held against an object with an axial force above a threshold value, wherein the member comprises a deformable link for holding the piercing tip in the cutting position while the insertion force is placed on the piercing tip, the deformable link having a first configuration when the piercing tip is in the cutting position and having a second configuration when the piercing tip is in the shielded position; and at least one spring for retracting the piercing tip from the cutting position to the shielded position;

wherein the catch releasably maintains the deformable link in the first configuration and said at least one spring applies a bias force on said link such that when the insertion force is below the threshold value, upon release of the axial insertion force placed on the piercing tip while the piercing tip is in the cutting position, the link moves from the first configuration to the second configuration and the piercing tip moves to the shielded position.

12. The retracting tip assembly of claim 6, wherein the spring comprises a torsion spring.

13. The retracting tip assembly of claim 1, wherein the ends of the first and second links not pivotally connected to one another are closer together when the piercing tip moves to the shielded position.

14. The retracting tip assembly of claim 1, further comprising a latch arm on one of the links for manually moving the links to the first configuration, the trocar handle housing including catch means for holding the latch arm in an armed position at which the piercing tip is in the cutting position.

15. The retracting tip trocar assembly of claim 14, wherein one end of the latch arm is connected to one of the links and the other end thereof extends outwardly of the trocar handle, the catch means comprising a curved slot in the trocar handle, the latch arm being movable along the curved slot, the curved slot terminating in an enlarged opening formed in part by a support surface against which the latch arm presses when the piercing tip is in an armed position.

16. The retracting tip assembly of claim 15, wherein the piercing tip is located further outside the distal end of the trocar tube in the armed position than when the piercing tip is in the cutting position.

17. The retracting tip assembly of claim 16, wherein the latch arm automatically moves from the support surface to a position in alignment with the curved slot when the piercing tip is pushed against an object.

18. The retracting tip assembly of claim 1, wherein the trocar handle housing includes a track and the obturator has a shaft which includes a slider, the slider cooperating with the track to guide the shaft axially along the trocar tube.

19. The retracting tip assembly of claim 6, wherein the torsion spring comprises a wire having first and second arms extending from a coiled portion of the wire, the first arm pressing against the first link and the second arm pressing against the second link.

20. A method of puncturing a wall of a human body cavity, comprising the steps of:

providing a retractable tip trocar assembly having an elongated trocar obturator extending in an axial direction and having a proximal end and a piercing tip at a distal end thereof, an elongated trocar tube in which the trocar obturator is housed such that the piercing tip is movable in the axial direction from a cutting position at which the piercing tip is outside the trocar tube to a shielded position at which the piercing tip is entirely within the trocar tube, a trocar handle housing which receives the proximal end of the elongated trocar obturator and which includes a catch, retracting means mounted within a trocar handle housing for retracting the piercing tip from the cutting position to the shielded position, a first link pivotally attached to the trocar obturator and to a second link, the second link being pivotally attached to the trocar handle housing, the links being in a first configuration when the piercing tip is in the cutting position and the links being in a second configuration when the piercing tip is in the shielded position, the retracting means acting on at least one of the first and second links;

placing the links in the first configuration with the piercing tip in the cutting position; and piercing a wall of a human body cavity by manually pushing the piercing tip against the wall of the human body cavity until the piercing tip punctures the wall, thereby triggering the retracting means to move the links to the second configuration and withdraw the piercing tip entirely into the trocar tube.

21. The method of claim 20, further comprising a step of insufflating the human body cavity.

22. The method of claim 21, wherein the insufflating step is performed prior to the piercing step.

23. The method of claim 20, wherein one end of said first link is pivotally attached to a proximal end of said trocar obturator, another end of said first link is pivotally attached to an end of said second link, and another end of said second link is pivotally attached to said trocar housing.

24. A method of puncturing a wall of a human body cavity, comprising the steps of:

providing a retractable tip trocar assembly having;

an elongated trocar obturator extending in an axial direction and having a proximal end and a piercing tip at a distal end thereof, an elongated trocar tube in which the trocar obturator is housed such that the piercing tip is movable in the axial direction from a cutting position at which the piercing tip is outside the trocar tube to a shielded position at which the piercing tip is entirely within the trocar tube, retracting means mounted within a trocar handle housing for retracting the piercing tip from the cutting position to the shielded position, the trocar handle housing receiving the proximal end of the trocar obturator, a member, comprising links, movable from a first position at which the member prevents movement of the trocar obturator to a second position at which the member does not prevent movement of the trocar obturator, the member being held in the first position when the piercing tip is pressed against an object with an axial force above a threshold value, and biasing the member toward the second position by applying a bias force on the member such that when the insertion force is below the threshold value the member moves from the first position to the second position and the piercing tip moves to the shielded position;

placing the links in a straight configuration with the piercing tip in the cutting position;

piercing a wall of a human body cavity by manually pushing the piercing tip against the wall of the human body cavity until the piercing tip punctures the wall, thereby triggering movement of the links to a bent configuration and withdrawing the piercing tip entirely into the trocar tube;

wherein the trocar assembly includes a trocar handle housing which receives the proximal end of the elongated trocar obturator, and the retracting means is mounted within the trocar handle housing and includes at least one spring for biasing the links toward the bent configuration, the links being extendible to a straight configuration, and the trocar assembly includes a latch arm mounted to at least one of the links and extending through a slot in the housing, the slot defining a catch;

the step of placing the links in the straight configuration comprising moving the latch arm along the slot to extend the links to the straight configuration and engaging the latch arm with the catch to hold the piercing tip in the cutting position.

25. The method of claim 24, wherein the housing includes an upper housing and a lower housing, the trocar obturator and retracting means being supported by the upper housing and the upper housing being separable from the lower housing, the lower housing including a valve for automatically sealing the trocar tube when the trocar obturator is removed from the trocar tube, the method further comprising a step of separating the upper housing from the lower housing such that the trocar tube is sealed by the valve, the separating step being performed after the piercing step is performed.

26. The method of claim 24, wherein the latch arm is flexible and is automatically disengaged from the catch during the piercing step due to axial movement of the link means when an insertion load force is placed on the piercing tip.

27. The method of claim 24, wherein one end of said first link is pivotally attached to a proximal end of said trocar obturator, another end of said first link is pivotally attached to an end of said second link, and another end of said second link is pivotally attached to said trocar housing.

28. A method of puncturing a wall of a human body cavity, comprising the steps of:

providing a retractable tip trocar assembly having:

an elongated trocar obturator extending in an axial direction and having a proximal end and a piercing tip at a distal end thereof, an elongated trocar tube in which the trocar obturator is housed such that the piercing tip is movable in the axial direction from a cutting position at which the piercing tip is outside the trocar tube to a shielded position at which the piercing tip is entirely within the trocar tube, retracting means for retracting the piercing tip from the cutting position to the shielded position, a trocar handle housing which receives the proximal end of the elongated trocar obturator, the retracting means being mounted in the trocar handle housing, a member which includes a first link pivotally attached to the proximal end of the trocar obturator and to a second link, the second link being pivotally attached to the trocar handle housing, the links being in a first configuration when the piercing tip is in the cutting position and the links being in a second configuration when the piercing tip is in the shielded position, the retracting means acting on at least one of the links and the links being held in the first configuration when the piercing tip is pressed against an object with an axial force above a threshold value;

biasing the links toward the second configuration, the biasing means applying a bias force on the links such that when the insertion force is below the threshold value, the links move from the first configuration to the second configuration and the retracting means moves the piercing tip to the shielded position;

placing the links in the first configuration with the piercing tip in the cutting position and the links in the first configuration;

piercing a wall of a human body cavity by manually pushing the piercing tip against the wall of the human body cavity with an axial force above the threshold value until the piercing tip punctures the wall and the axial force falls below the threshold value, whereupon the retracting means moves the links to the second configuration to withdraw the piercing tip entirely into the trocar tube.

29. The method of claim 28, wherein one end of said first link is pivotally attached to a proximal end of said trocar obturator, another end of said first link is pivotally attached to an end of said second link, and another end of said second link is pivotally attached to said trocar housing.

30. The method of claim 28, wherein the links are in a straight configuration in the first configuration, the housing has a slot therein, and the member includes a latch arm extending through the slot in the housing, the slot having a catch and the step of placing the links in the first configuration comprising moving the latch arm along the slot to extend the links to the straight configuration and engaging the latch arm with the catch to hold the piercing tip in the cutting position.

31. The method of claim 30, wherein the housing includes an upper housing, having the slot therein, and a lower housing, the trocar obturator and retracting means being supported by the upper housing and the upper housing being separable from the lower housing, the lower housing including a valve for automatically sealing the trocar tube when the trocar obturator is removed from the trocar tube, the method further comprising a step of separating the upper housing from the lower housing such that the trocar tube is sealed by the valve, the separating step being performed after the piercing step is performed.

32. The method of claim 30, wherein the latch arm is flexible and there is included a step of automatically disengaging the latch arm from the catch during the piercing step due to axial movement of the links when an insertion force is placed on the piercing tip.

33. The method of claim 28, further comprising a step of insuring the human body cavity.

34. The method of claim 33, wherein the insufflating step is performed prior to the piercing step.

* * * * *